United States Patent [19]
Lin

[11] Patent Number: 5,930,327
[45] Date of Patent: Jul. 27, 1999

[54] X-RAY IMAGE PROCESSING

[75] Inventor: Zhongmin Lin, Danbury, Conn.

[73] Assignee: Trex Medical Corporation, Danbury, Conn.

[21] Appl. No.: 08/880,978

[22] Filed: Jun. 23, 1997

[51] Int. Cl.$^6$ .................................................. G01N 23/04
[52] U.S. Cl. .............................................. 378/62; 378/37
[58] Field of Search ...................... 378/37, 62; 382/132, 382/128

[56] References Cited

U.S. PATENT DOCUMENTS

| | | | |
|---|---|---|---|
| 4,907,156 | 3/1990 | Doi et al. | 382/130 |
| 5,268,967 | 12/1993 | Jang et al. | 382/6 |
| 5,452,367 | 9/1995 | Bick et al. | 382/128 |
| 5,572,565 | 11/1996 | Abdel-Mottaleb | 378/37 |
| 5,579,360 | 11/1996 | Abdel-Mottaleb | 378/37 |
| 5,627,907 | 5/1997 | Gur et al. | 382/132 |

OTHER PUBLICATIONS

Asaga, T. et al., "Breast Imaging: dual–energy projection radiography with digital radiography", *Radiology* (United States), Sep. 1987, 164(3) pp. 869–870, ISSN 0033–8419.

Chan, HP., et al., "Digital Mammography. ROC studies of the effects of pixel size and unsharp–mask filtering on the detection of subtle microcalcifications", *Invest Radiol*, (United States), Jul. 1987, 22(7) pp. 581–589, ISSN 0020–9996.

Chan, HP. et al., "Image feature analysis and computer–aided diagnosis in digital radiography. 1. automated detection of microcalcifications in mammography", *Med Phys* (United States), Jul.–Aug. 1987, 14(4) pp. 538–548, ISSN 0094–2405.

Chan, HP et al., "Digital mammography: development of a computer–aided system for detection for microalcifications", *The International Society for Optcial Engineering*, vol. 767, pt. 1, pp. 367–370, Medical Imaging 1987.

Heang–Ping et al., "Digital characterization of clinical mammographic microcalcifications: applications in computer–aided detection", *The International Society for Optical Engineering*, vol. 914, pt. A, pp. 591–593. 1988.

Sommer, FG et al. "Digital processing of film radiographs", *AJR Am J Roentgenol*, (United States), Jan. 1985 144 (1) pp. 191–196, ISSN 0361–803X.

Schneider et al., "Application of Optical Instrumentation in Medicine XIV and Picture Archiving and Communication Systems (PACS IV) for Medical Applications", *The International society for Optical Engineering*, vol. 626, Feb. 2–7, 1986, pp. 347–348.

Zbou et al., "Geometric Unwarping for Digital Subtraction Mammography", *The University of Manitoba*, pp. 25–30, No Date.

Gonzalez et al., Digital Image Processing, 1993, Addison–Wesley publishing Company, pp. 171–180, 167–169, 196–197 & 418–420 no month.

Jang et al., "Image Enhancement for Computer Radiographic Images," 0–8194–1782–3/95/$6.00. 2434:278–289 1995 no month.

Liu et al., "Edge enhancement to improve visualizations of tube/line placement in X–ray imaging," 0–8194–1782–3/95/$6.00, SPIE 2434:274–277 1995 no month.

*Primary Examiner*—David P. Porta
*Assistant Examiner*—David Vernon Bruce
*Attorney, Agent, or Firm*—Fish & Richardson P.C.

[57] ABSTRACT

An object to be imaged is positioned between an x-ray source and an x-ray imager. The x-ray source is operated to direct x-rays through and around the object. Electrical signals representative of the intensity of the x-rays impinging on the x-ray imager are used to locate a boundary of the object, and an x-ray image is generated using this boundary. Alternatively or additionally, an x-ray image is generated using the highest frequency magnitude in the set of electrical signals.

51 Claims, 9 Drawing Sheets

X-RAY IMAGE PROCESSING

BACKGROUND OF THE INVENTION

The invention relates to the enhancement of a digital x-ray image, such as an x-ray image of the breast ("a mammogram").

A mammogram reveals aspects of the internal structure of a human breast in order to facilitate the early detection of abnormalities within the breast. In x-ray mammography, x-rays are directed through the breast, which may be composed of various types of tissue, e.g., healthy glandular and/or fatty tissue, and/or abnormal tissue such as tumors and/or microcalcifications.

Different tissue types can have different densities. Denser tissue attenuates x-rays more than less-densesue. The ability to discriminate between tissues having relatively close densities can facilitate the detection of abnormal or suspicious lesions in the breast while such lesions are still small, in their incipiency.

The attenuated x-rays are then captured to generate a mammogram. In some systems, a sheet of photosensitive film is placed behind the breast. After exposure, the film is developed and viewed for diagnosis. Other systems employ an electrical imager to convert the x-rays into electrical signals, or image data, which may be printed, e.g., on a laser printer for diagnosis.

SUMMARY OF THE INVENTION

In one aspect of the invention, an object to be imaged is positioned between an x-ray source and an x-ray imager. The x-ray source is operated to direct x-rays through and around the object. Electrical signals representative of the intensity of the x-rays impinging on the x-ray imager are used to locate a boundary of the object, and an x-ray image is generated using this boundary.

Among other advantages, this aspect of the invention allows, e.g., the electrical signals representative of the region inside the boundary to be processed in whole or in part independently of the electrical signals representative of the region outside the boundary. Not only can this increase processing speed, but it can also reduce if not eliminate the extent to which electrical signals representative of the region outside of the boundary influence the processing of the electrical signals representative of the region inside of the boundary.

Embodiments of this aspect of the invention can include the following features. The electrical signals can comprise an array of digital values. The boundary of the object (e.g., the skin boundary of a breast) can be located by calculating the maximum gradient of the digital values along each line of the array. The boundary value is found by averaging the set of digital values in the array that correspond to the boundary of the object. Those digital values in the array that equal or exceed the boundary value are set equal to the boundary value, and the mean and standard deviation of those values that fall below the boundary value are calculated. A sigmoid transformation having a range with a median determined by the calculated mean (e.g., a range with a median equal to 0.95 times the calculated mean), and a slope determined by the calculated standard deviation (e.g., a slope equal to 1.2 times the calculated standard deviation), is then applied to this latter set of digital values. The outputs of the sigmoid transformation function are then multiplied by an integer constant to form an intermediary output set, and the minimum value of the intermediary output set is subtracted from each member of the set. An output set is produced by scaling the intermediary output set to a range of output values suitable for output on an output device.

The range of the digital values in the array can also be compressed (e.g., with a logarithmic function) and/or filtered. Filtering can be used to filter low spatial frequencies from the digital values, such as by applying unsharp masking. A first mask (e.g., with a kernal size of 100×100) can be generated from the digital values, and a second mask (e.g., with a kernal size of 75×75) can be generated from the first mask. The second mask can then be multiplied by a constant (e.g., 0.55) and subtracted from the digital values to yield a set of masked data.

In another aspect of the invention, an object to be imaged is positioned between an x-ray source and an x-ray imager. The x-ray source is operated to direct x-rays through the object, and electrical signals associated with a region of the x-ray imager, and having a magnitude representative of the intensity of the x-rays impinging on such region, are generated. An x-ray image is generated using the highest frequency magnitude in the set of electrical signals.

Among other advantages, this aspect of the invention allows, e.g., the range of the electrical signal to be spread over the available resolution to enhance image detail, and/or to create image data suitable for output on an output device.

Embodiments of this aspect of the invention can include the following features. The highest frequency magnitude can be identified by generating a histogram of the magnitudes of the electrical signals in the set. A threshold magnitude value can be calculated by determining MaxFrequency, the frequency corresponding to the highest frequency magnitude, dividing MaxFrequency by approximately 1000 to determine LowFrequency, and subtracting approximately 300 from the magnitude corresponding to LowFrequency. The threshold magnitude value can then be subtracted from the magnitudes of the electrical signals in the set.

Other advantages and features will become apparent from the following description of the preferred embodiments and from the claims.

DETAILED DESCRIPTION

Figure 1:
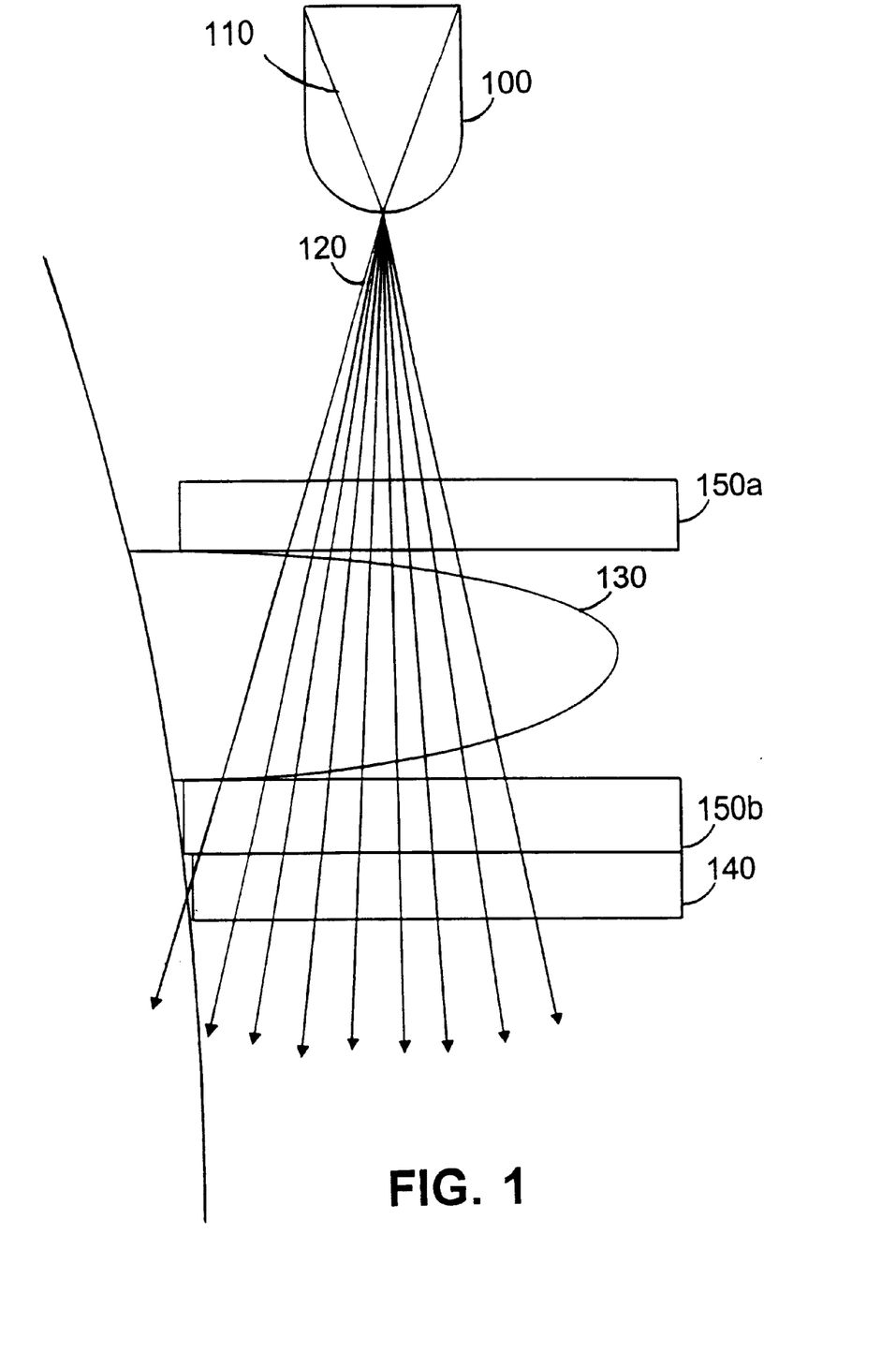
FIG. 1 is a schematic diagram of a mammography apparatus.

In the image acquisition phase of digital mammography, an x-ray source 100 containing an x-ray tube 110 directs x-rays 120 through and around a human breast 130 compressed by compression paddles 150*a*–*b*. The x-ray source 100 can be positioned above the breast 130, such that it directs x-rays 120 downward through and around the breast 130. A digital imager 140 containing one or more detectors lies underneath the breast 130. The output of the imager is used to create an x-ray image of the breast.

Figure 2:
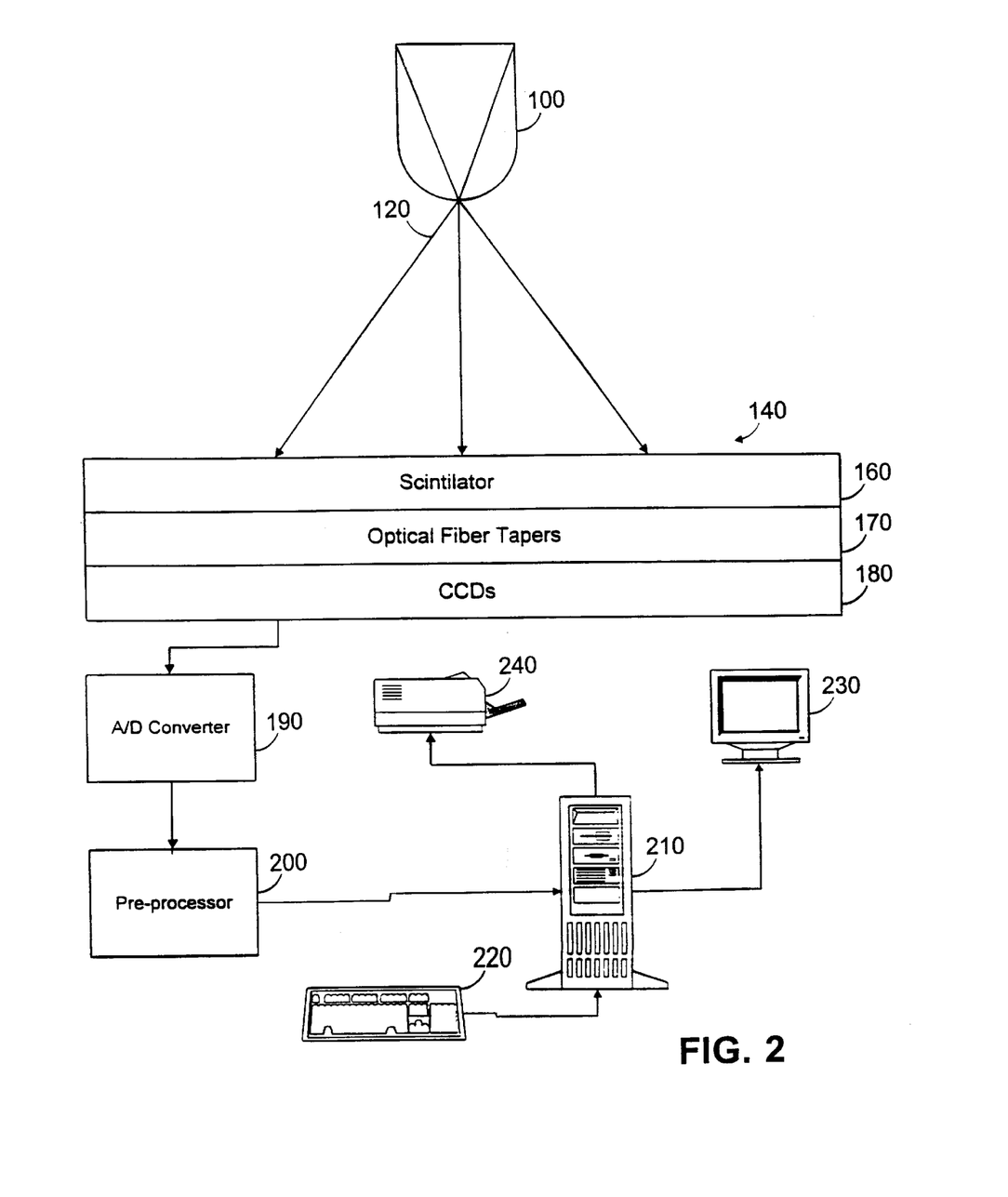
FIG. 2 is a schematic diagram of an apparatus for collecting and essing image data for a digital mammogram.
Figure 3:
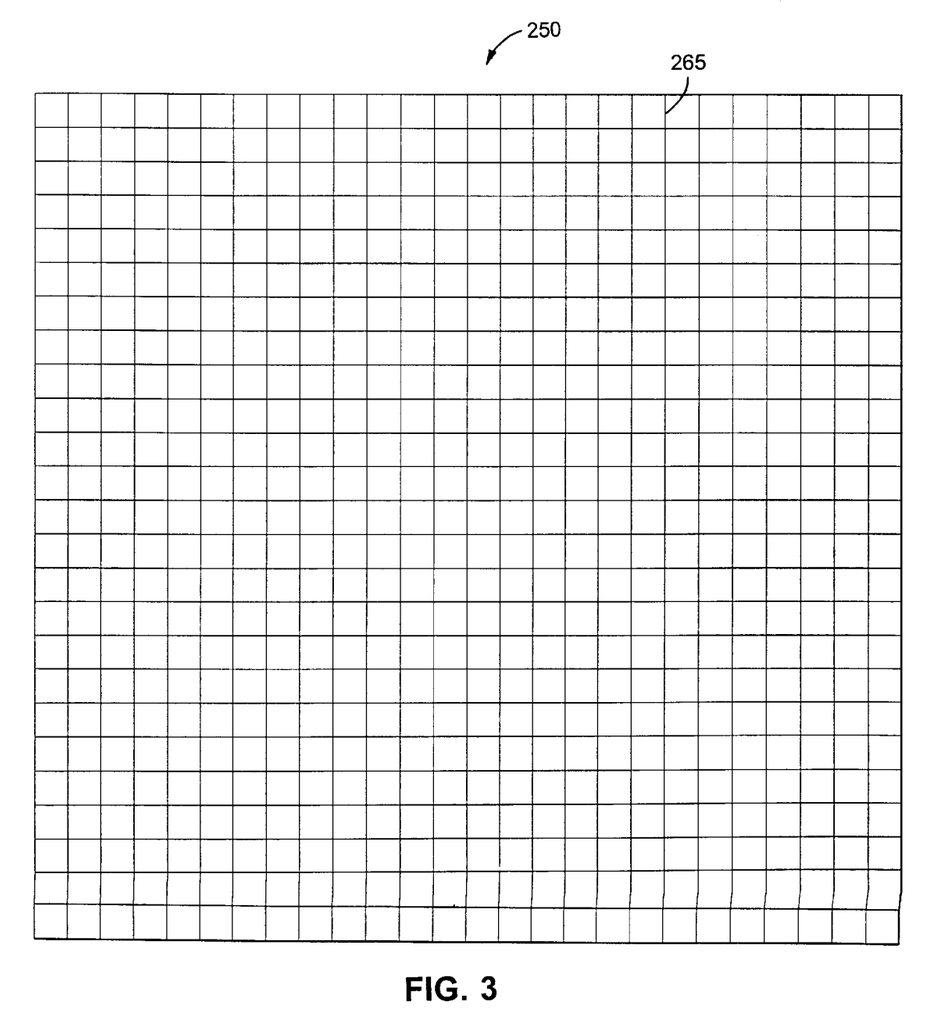
FIG. 3 is a schematic diagram of a mammogram space comprising a two-dimensional array of pixels.

As shown in FIG. 2, the digital imager 140 contains a scintillator 160, a layer of optical fiber tapers 170, and a layer of charge-coupled devices (CCDs) arranged in a two-dimensional array 180. Each CCD contains a grid of light-sensitive elements, each corresponding to a pixel 265 in the resultant mammogram image 250 (FIG. 3). (For ease of illustration, the breast image is not shown in FIG. 3.) The size of each element on a typical CCD is approximately 40×40 microns.

During imaging, the x-ray tube 110 is energized to direct x-rays 120 through and around the breast 130. Some x-rays may be scattered by the breast.

After passing through and around the breast 130, the x-rays 120 hit the scintillator 160 in the imager 140, causing it to emit visible light. The visible light passes through the optical fiber tapers 170 to the CCD arrays 180. Each light-sensitive element in the CCD array outputs a voltage corresponding to the intensity of the light striking the region of the element. However, not all CCD elements respond identically to the same x-ray intensity. Although this is in part accounted for by "white field correction," some elements typically saturate at lower exposures than others.

The imager 140 transmits the output voltage data from the CCDs 180 to an analog-to-digital converter 190, which converts the data into digital form. These digital image data may then optionally pass through a pre-processor 200 to perform, e.g., de-warping, seaming (e.g., to combine the data from the separate CCDs into a single two-dimensional array of image data), defect mapping, and white fielding. The total resolution of the resulting image 250 may be, e.g., 4800×6400 pixels. The data are then sent to a computer workstation 210 running software implementing the routines described below. The computer 210 is typically attached to a keyboard 220 or other input device. When the computer has completed processing the image data, the processed data may be displayed on a monitor 230, printed on a printer 240, or stored on a hard disk or other persistent medium.

The image data that the computer 210 receives from the pre-processor 200 typically has a range of approximately 14 bits. Each image datum corresponds to a single pixel 265 in the mammogram image 250. The algorithm on computer 210 assigns a Cartesian coordinate system to the data set, with the origin in the upper-left corner of the image, x increasing to the right, and y increasing down. The invention, though, is not dependent on any particular pixel coordinate system. Additionally, although the algorithm described herein assumes that the breast is oriented horizontally, pointing toward the right, the algorithm can be modified to work with breasts in different orientations.

The algorithm first locates a "breast skin boundary," and calculates therefrom a "breast boundary value." The breast skin boundary does not necessarily correspond to the true geometric boundary of the breast, but rather is a surrogate for that contour. The breast boundary value is the mean intensity of the image data points that lie on the breast skin boundary.

Figure 4:
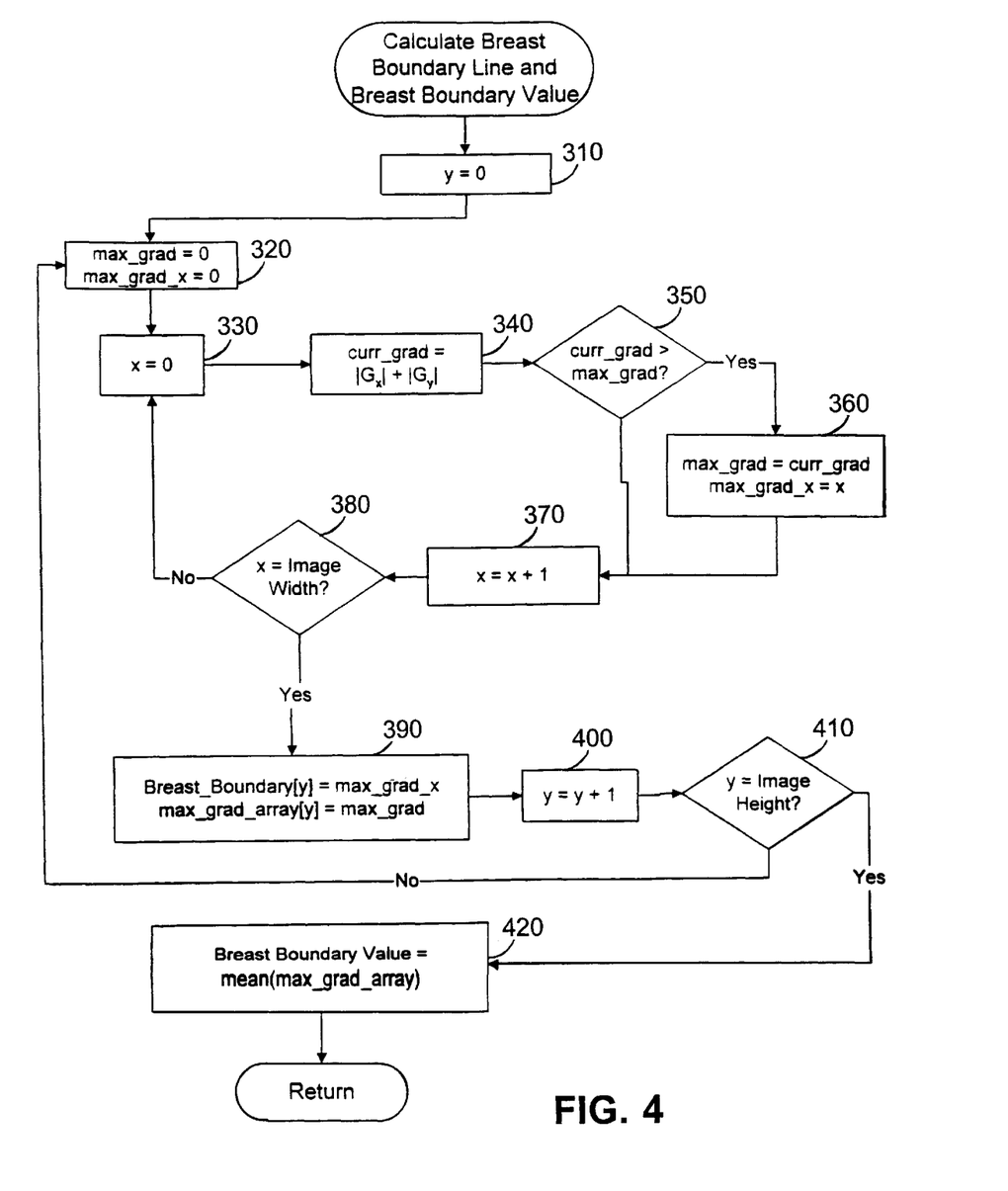
FIG. 4 is a flow diagram of a computer-implemented method for locating a breast skin line in the image data, and for calculating a breast boundary value therefrom.

FIG. 4 is a flow diagram of a computer-implemented routine for locating the breast skin boundary, and for calculating the breast boundary value.

The routine locates the pixel in each row of image data that has the highest intensity gradient along the row, and identifies the breast skin boundary as the locus of all such pixels. The routine first initializes a local row index variable y to zero (step 310). A local variable max_grad indicating the maximum gradient encountered so far on row y is also initialized to zero, as is a local variable max_grad_x indicating the x position of the pixel corresponding to max_grad.

The maximum gradient along row y is found in steps 340–380. Specifically, in step 340, the gradient of the pixel at coordinate x,y is calculated by using the Sobel operators to approximate $|G_x|+|G_y|$ (step 340). If the gradient at x,y is greater than the value stored in max_grad (the previous maximum gradient), then max_grad is set to the gradient at x,y, and max_grad_x is set to x (step 350, 360). The process is repeated for every pixel in row y (steps 370, 380).

After the maximum gradient (max_grad), and its corresponding x coordinate (max_grad_x), of row y have been found, the value of max_grad is stored in max_grad_array, and the coordinates of the pixel (max_grad_x, y) is added to the Breast_Boundary array, which stores the set of pixels corresponding to the breast skin boundary (step 390). The y variable is incremented by 1 (step 400), and the process repeats for all rows (step 410).

When the method has processed each row in the image, the breast boundary value is calculated as the mean of the values stored in max_grad_array (step 420).

Figure 5:
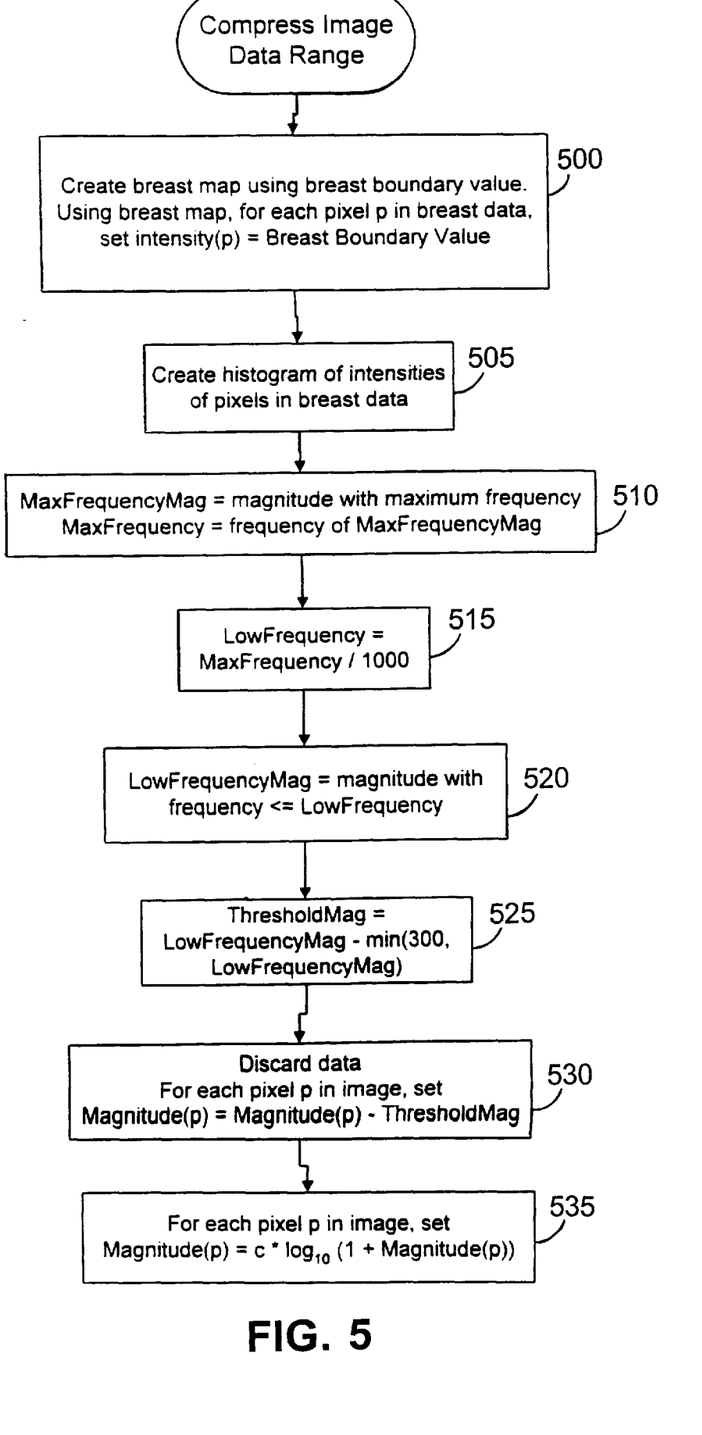
FIG. 5 is a flow diagram of a computer-implemented method for compressing the range of the image data.

After the breast skin boundary and the breast boundary value have been calculated, the algorithm compresses the range of the image data. A routine for performing this compression is shown in FIG. 5. First, a breast map is created to classify each datum in the image data as a breast datum or a non-breast datum (step 500). Specifically, if the magnitude of an image datum is greater than the breast boundary value, that image datum is classified as a non-breast datum. The remaining image data are classified as breast data. Using the breast map, the magnitude of each non-breast datum is then set to the breast boundary value (step 500). This effectively creates a homogeneous field outside of the breast.

Figure 6:
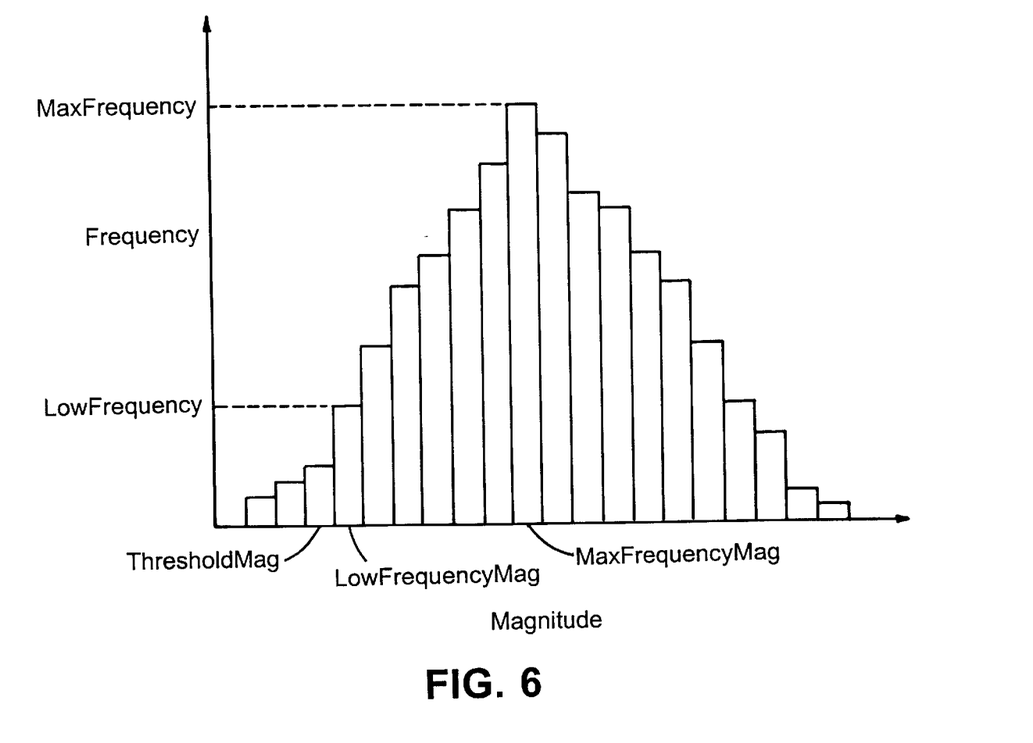
FIG. 6 is a schematic of a histogram generated by the routine of FIG. 5.

A histogram of the breast data, shown in FIG. 6, is then computed, indicating the number of breast data points at each magnitude (step 505). (For ease of illustration, only a few data points are shown in FIG. 6.)

Data below a threshold frequency are then discarded, and the remaining data shifted in steps 510–530. Specifically, in step 510, the highest point in the histogram computed in step 505 is located to identify both (1) the magnitude exhibited by the greatest number of breast data points (i.e., the highest frequency magnitude), and (2) the number of breast data points that exhibit that magnitude (i.e., the highest frequency). This latter value is assigned to variable MaxFrequency (FIG. 6). A variable LowFrequency is then computed as MaxFrequency/1000 (step 515). Again using the histogram, the magnitude corresponding to LowFrequency is determined. This magnitude is assigned to the variable LowFrequencyMag (step 520). ThresholdMag is then calculated as LowFrequencyMag minus the lesser of 300 and LowFrequencyMag (step 525). Data points with a magnitude less than ThresholdMag are discarded. The data range is then shifted by subtracting ThresholdMag from each of the remaining data points (i.e., those data points having a magnitude greater than ThresholdMag) (step 530). A logarithmic function with floating point output is then applied to the shifted data (step 540).

Next, unsharp masking is used to filter low spatial frequencies from the image data, enhancing image detail. Generally, the unsharp masking routine creates a mask image of a source image, and then subtracts a function of the mask image from the source image, creating a result image. The value of a mask image at coordinates x,y is equal to the mean value of the source image data within an area (the "kernal") centered on coordinates x,y.

Figure 7:
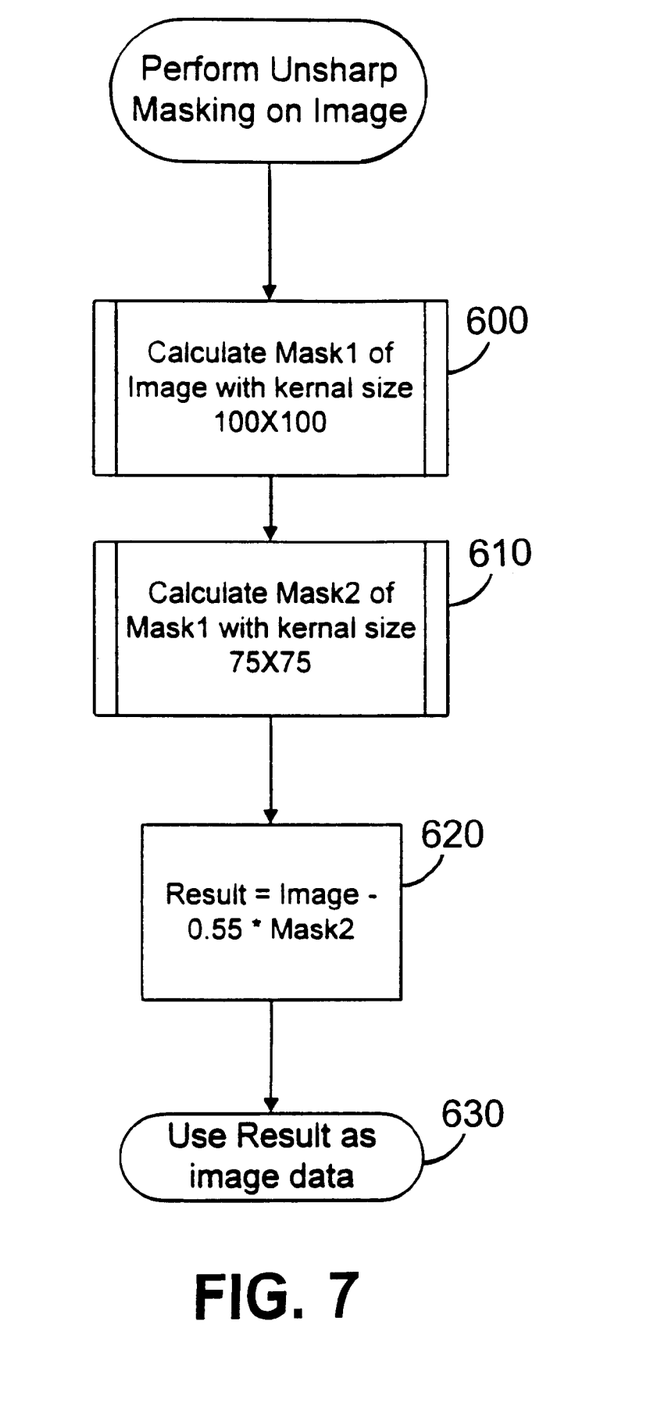
FIG. 7 is a flow diagram of a computer-implemented method for applying unsharp masking to image data.
Figure 8:
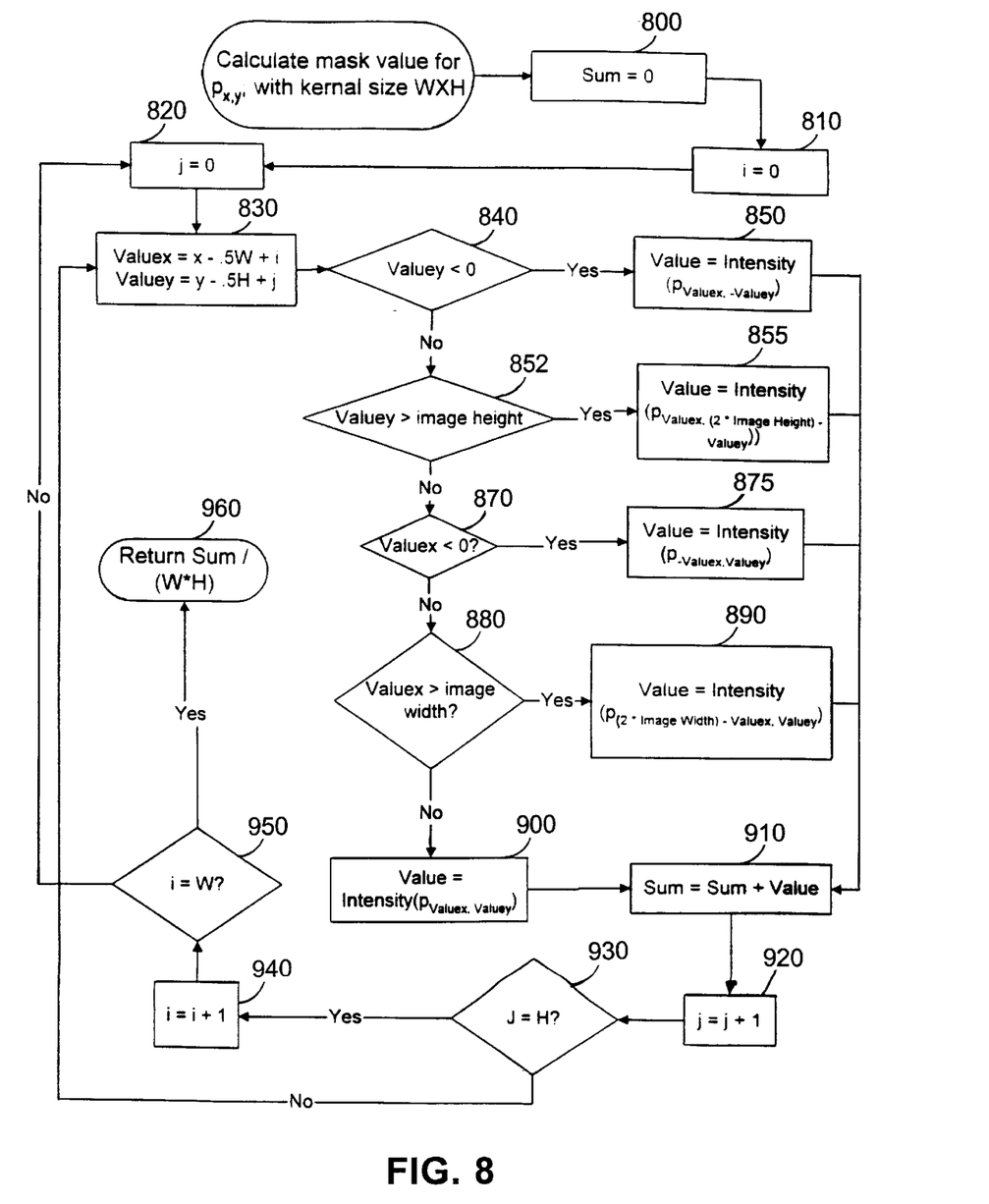
FIG. 8 is a flow diagram of a computer-implemented method for calculating the mask value in the unsharp masking routine of FIG. 7.

FIG. 7 is a flow diagram of a computer-implemented routine for applying unsharp masking to the image data. First, a mask Mask1 is created from the image data using a kernal size of 100×100 pixels (step 600). FIG. 8, described below, is a flow diagram of a computer-implemented routine for calculating mask values. Next, a mask Mask2 is created from Mask1 by using a kernal size of 75×75 pixels. (step 610). Then, a result image Result is obtained by subtracting Mask2 multiplied by 0.55 from the image data (step 620). Result is used as the image data by all subsequent routines (step 640).

As shown in FIG. 8, the routine for calculating mask values takes as inputs the x and y coordinates of the desired mask value, and a kernal size represented by a width W and a height H. The routine begins by initializing the variables Sum, i, and j to zero (steps 800, 810, 820). The variable Sum is used to track the sum of the data points within the kernal. The variables i and j are used to track the x and y coordinates, respectively, of the data points in the kernal.

The routine first calculates the coordinates of the starting point in the kernal (i.e., the upper left hand of the kernal) (step 830). If this point is outside of the image boundaries, then the routine instead uses the mirror image of the point within the image boundaries (steps 840–890).

The intensity of the point (either the actual point or its mirror image if the actual point lies outside the image boundaries) is then found in step 900. This intensity is added to the running sum of intensities (step 910). The process is repeated for each point in the kernal (steps 930, 940, 950). Finally, the mean value of the intensities is returned as the mask value for the specified coordinate (step 960).

Figure 9:
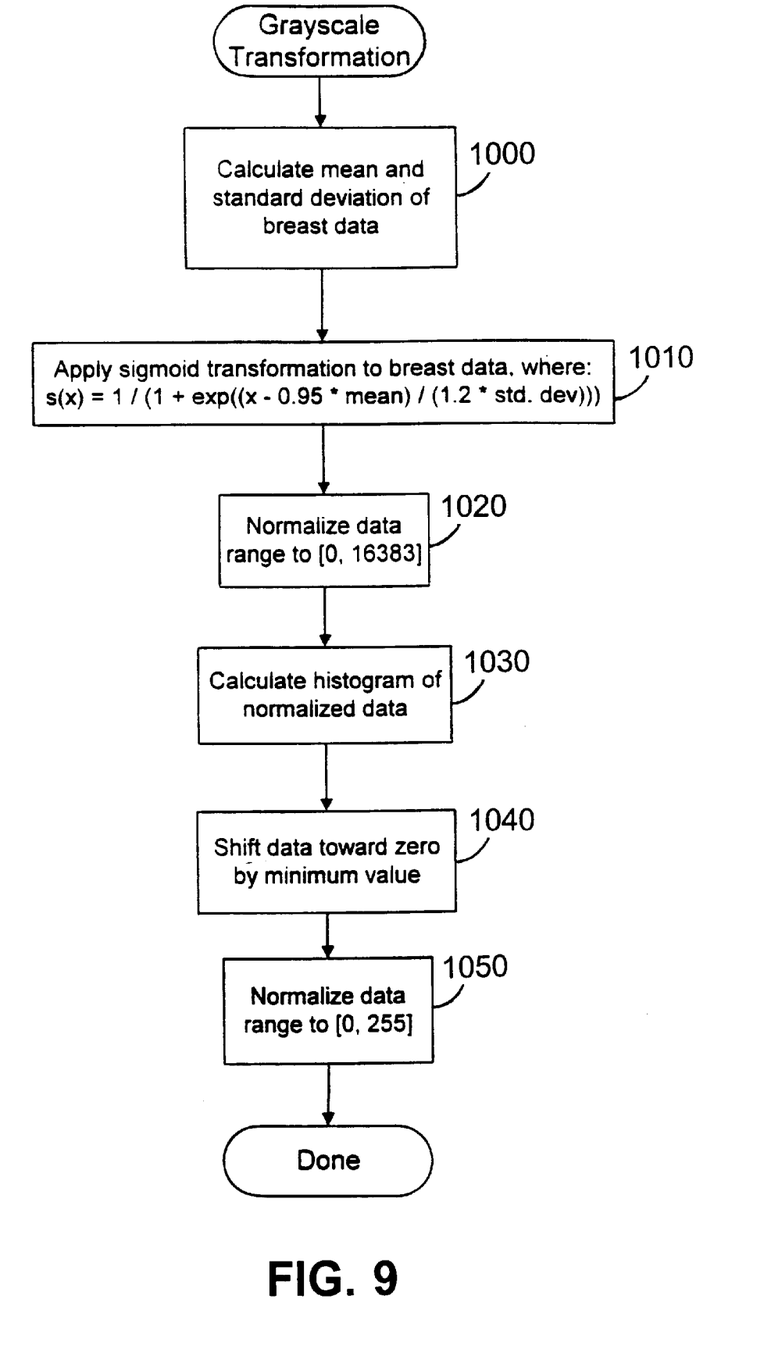
FIG. 9 is a flow diagram of a computer-implemented method for performing a grayscale transformation on the image data.

After low spatial frequencies are filtered from the image by the FIG. 7 unsharp masking routine, the result image data (Result) are transformed into data with a range of 256 gray levels, ranging from zero to 255, making it suitable for output on conventional laser printers and other output devices. FIG. 9 is a flow diagram of this process. First, the mean and standard deviation of the result image data (Result), minus the non-breast data identified in step 500, are calculated (step 1000).

A sigmoid transformation function, with the calculated mean and standard deviation as parameters, is then applied to the image data (step 1010). Specifically, the range of the sigmoid transformation function has a median equal to 0.95 times the mean, and the slope of the function is set equal to 1.2 times the standard deviation. The resulting data are also normalized to an integer range of [0, 16383] by multiplying each resulting value by 16383 (step 1020). A histogram of the normalized data is then calculated (step 1030), and the data are shifted towards zero by subtracting the minimum data value from each data value (step 1040). Finally, the shifted data are normalized to an integer range of [0, 255] (step 1050).

The resulting image data may then be sent to a laser printer or other suitable output device, or stored in a file on a hard disk drive or on other storage medium.

Other embodiments include use of an imager using a single flat panel detector composed of an array of pixels. Instead of or in addition to unsharp masking, a Fourier Transformation can be used to filter low spatial frequencies from the image data.

Although the invention is described in terms of a software implementation, the invention may be implemented in software or hardware or firmware, or a combination of the three.

The present invention is not limited to the embodiment depicted and described. Rather, the scope of the invention is defined by the claims.

What is claimed is:

1. A method for generating an x-ray image of an object, the method comprising:

positioning the object between an x-ray source and an x-ray imager;

operating the x-ray source to direct x-rays through and around the object to the x-ray imager, whereby the intensity of the x-rays impinging on the x-ray imager varies over the surface of the x-ray imager;

generating electrical signals representative of the intensity of the x-rays impinging on the x-ray imager;

locating a boundary of the object using the electrical signals;

determining a boundary value from the boundary of the object;

processing electrical signals in accordance with the boundary value;

generating an x-ray image using the processed electrical signals.

2. The method of claim 1 wherein the object is a breast.

3. The method of claim 2 wherein locating the boundary of the object comprises locating the boundary of the skin of the breast.

4. The method of claim 1 wherein the electrical signals comprise an array of digital values.

5. The method of claim 4 wherein locating the boundary of the object comprises calculating the gradient of each of a plurality of values along a line of the array.

6. The method of claim 4 wherein generating the x-ray image comprises compressing the range of the digital values.

7. The method of claim 4 wherein generating the x-ray image comprises filtering the digital values.

8. The method of claim 7 wherein filtering the digital values comprises filtering low spatial frequencies from the digital values.

9. The method of claim 4 wherein locating the boundary of the object comprises selecting a set of digital values in the array corresponding to the boundary of the object.

10. The method of claim 9 wherein determining the boundary value comprises applying a function to the digital values in the set.

11. The method of claim 10 wherein the function comprises averaging the digital values in the set.

12. The method of claim 4 wherein locating the boundary of the object comprises determining the maximum gradient of the digital values along a line of the array.

13. The method of claim 12 wherein locating the boundary of the object comprises determining the maximum gradient of the digital values along each of a plurality of lines of the array.

14. The method of claim 13 wherein the step of locating the boundary of the object comprises determining the maximum gradient of the digital values along each line of the array.

15. The method of claim 4 wherein processing electrical signals in accordance with the boundary value comprises setting digital values in the array to a value corresponding to the boundary value.

16. The method of claim 15 wherein processing electrical signals in accordance with the boundary value comprises:

identifying digital values in the array that equal or exceed the boundary value;

setting the identified digital values to a value corresponding to the boundary value.

17. The method of claim 16 wherein processing electrical signals in accordance with the boundary value comprises setting the identified digital values to the boundary value.

18. The method of claim 15 wherein processing electrical signals in accordance with the boundary value comprises identifying digital values in the array that are less than the boundary value.

19. The method of claim 18 wherein processing electrical signals in accordance with the boundary value comprises:

calculating the mean and standard deviation of the identified digital values;

applying a sigmoid transformation to the identified digital values, the sigmoid transformation function having a range with a median derived from the calculated mean and a slope derived from the calculated standard deviation.

20. The method of claim 19 wherein the median of the range of the sigmoid transformation is 0.95 times the calculated mean.

21. The method of claim 19 wherein the slope of the sigmoid transformation is 1.2 times the calculated standard deviation.

22. The method of claim 19 wherein generating the x-ray image comprises:

forming an intermediary output set by multiplying the outputs of the sigmoid transformation function by an integer constant;

subtracting the minimum value of the intermediary output set from each member of the intermediary output set;

producing an output set by scaling the intermediary output set to a range of output values suitable for output on an output device.

23. A method for generating an x-ray image of an object, the method comprising:

positioning the object between an x-ray source and an x-ray imager;

operating the x-ray source to direct x-rays through and around the object to the x-ray imager, whereby the intensity of the x-rays impinging on the x-ray imager varies over the surface of the x-ray imager;

generating an array of digital values representative of the intensity of the x-rays impinging on the x-ray imager;

selecting a set of digital values in the array corresponding to a boundary of the object;

generating an x-ray image by averaging the digital values in the set and using the averaged digital values to calculate a boundary value.

24. The method of claim 23 wherein generating the x-ray image comprises:

identifying the digital values in the array that equal or exceed the boundary value;

setting the identified digital values to the boundary value.

25. The method of claim 23 wherein generating the x-ray image comprises:

identifying the digital values in the array that are less than the boundary value;

calculating the mean and standard deviation of the identified digital values;

applying a sigmoid transformation to the identified digital values, the sigmoid transformation function having a range with a median derived from the calculated mean and a slope derived from the calculated standard deviation.

26. The method of claim 25 wherein the median of the range of the sigmoid transformation is 0.95 times the calculated mean.

27. The method of claim 25 wherein the slope of the sigmoid transformation is 1.2 times the calculated standard deviation.

28. The method of claim 25 wherein generating the x-ray image comprises:

forming an intermediary output set by multiplying the outputs of the sigmoid transformation function by an integer constant;

subtracting the minimum value of the intermediary output set from each member of the intermediary output set;

producing an output set by scaling the intermediary output set to a range of output values suitable for output on an output device.

29. A method for generating an x-ray image of an object, the method comprising:

positioning the object between an x-ray source and an x-ray imager;

operating the x-ray source to direct x-rays through the object to the x-ray imager, whereby the intensity of the x-rays impinging on the x-ray imager varies over the surface of the x-ray imager;

generating a set of electrical signals, each electrical signal being associated with a region of the x-ray imager, and having a magnitude representative of the intensity of the x-rays impinging on such region;

identifying the highest frequency magnitude in the set of electrical signals;

generating an x-ray image using the highest frequency magnitude.

30. The method of claim 29 wherein identifying the highest frequency magnitude comprises generating a histogram of the magnitudes of the electrical signals in the set.

31. The method of claim 29 wherein generating the x-ray image comprises determining a threshold magnitude value from the highest frequency magnitude.

32. The method of claim 31 wherein generating the x-ray image comprises subtracting the threshold magnitude value from the magnitudes of the electrical signals in the set.

33. The method of claim 31 wherein determining the threshold magnitude value comprises determining MaxFrequency, the frequency corresponding to the highest frequency magnitude.

34. The method of claim 33 wherein determining the threshold magnitude value comprises dividing MaxFrequency by a first constant to determine LowFrequency.

35. The method of claim 34 wherein the first constant is approximately one thousand.

36. The method of claim 34 wherein determining the threshold magnitude value comprises subtracting a second constant from the magnitude corresponding to LowFrequency.

37. The method of claim 36 wherein the second constant is approximately three hundred.

38. Apparatus for generating an x-ray image of an object, the apparatus comprising:

means for positioning the object between an x-ray source and an x-ray imager;

means for operating the x-ray source to direct x-rays through the object to the x-ray imager, whereby the intensity of the x-rays impinging on the x-ray imager varies over the surface of the x-ray imager;

means for generating a set of electrical signals, each electrical signal being associated with a region of the x-ray imager, and having a magnitude representative of the intensity of the x-rays impinging on such region;

means for identifying the highest frequency magnitude in the set of electrical signals;

means for generating an x-ray image using the highest frequency magnitude.

39. A method for generating an x-ray image of an object, the method comprising:

positioning the object between an x-ray source and an x-ray imager;

operating the x-ray source to direct x-rays through and around the object to the x-ray imager, whereby the intensity of the x-rays impinging on the x-ray imager varies over the surface of the x-ray imager;

generating an array of digital values representative of the intensity of the x-rays impinging on the x-ray imager;

locating a boundary of the object by determining the maximum gradient of the digital values along a line of the array;

generating an x-ray image using the boundary of the object.

40. The method of claim 39 wherein the boundary of the object comprises determining the maximum gradient of the digital values along each of a plurality of lines of the array.

41. The method of claim 40 wherein locating the boundary of the object comprises determining the maximum gradient of the digital values along each line of the array.

42. A method for generating an x-ray image of an object, the method comprising:

positioning the object between an x-ray source and an x-ray imager;

operating the x-ray source to direct x-rays through and around the object to the x-ray imager, whereby the intensity of the x-rays impinging on the x-ray imager varies over the surface of the x-ray imager;

generating an array of digital values representative of the intensity of the x-rays impinging on the x-ray imager;

locating a boundary of the object using the array of digital values;

generating an x-ray image using the boundary of the object and by applying a logarithmic function to the digital values to compress the range of the digital values.

43. A method for generating an x-ray image of an object, the method comprising:

positioning the object between an x-ray source and an x-ray imager;

operating the x-ray source to direct x-rays through and around the object to the x-ray imager, whereby the intensity of the x-rays impinging on the x-ray imager varies over the surface of the x-ray imager;

generating an array of digital values representative of the intensity of the x-rays impinging on the x-ray imager;

locating a boundary of the object using the array of digital values;

generating an x-ray image using the boundary of the object and by applying unsharp masking to the digital values to filter the digital values.

44. The method of claim 43 wherein applying unsharp masking to the digital values comprises generating a first mask from the digital values.

45. The method of claim 44 wherein first mask is generated from the digital values using a kernal size of approximately 100×100.

46. The method of claim 44 wherein applying unsharp masking to the digital values comprises generating a second mask from the first mask.

47. The method of claim 46 wherein applying unsharp masking to the digital values comprises multiplying the second mask by a constant, and subtracting the product from the array of digital values to generate a masked data set.

48. The method of claim 47 wherein the constant is approximately 0.55.

49. The method of claim 48 wherein the constant is 0.55.

50. The method of claim 46 wherein the second mask is generated from the first mask using a kernal size of approximately 75×75.

51. Apparatus for generating an x-ray image of an object, the apparatus comprising:

means for positioning the object between an x-ray source and an x-ray imager;

means for operating the x-ray source to direct x-rays through and around the object to the x-ray imager, whereby the intensity of the x-rays impinging on the x-ray imager varies over the surface of the x-ray imager;

means for generating electrical signals representative of the intensity of the x-rays impinging on the x-ray imager;

means for locating a boundary of the object using the electrical signals;

means for determining a boundary value from the boundary of the object;

means for processing electrical signals in accordance with the boundary value;

means for generating an x-ray image using the processed electrical signals.

* * * * *